United States Patent [19]

Fields et al.

[11] Patent Number: 5,600,870
[45] Date of Patent: Feb. 11, 1997

[54] ARTICULATING HINGE ASSEMBLY

[75] Inventors: Kyle D. Fields, El Dorado Hills; James P. Dudley, Sacramento, both of Calif.

[73] Assignee: OP-D-OP, Inc., Roseville, Calif.

[21] Appl. No.: 614,805

[22] Filed: Mar. 7, 1996

[51] Int. Cl.$^6$ .................................................. E05C 17/64
[52] U.S. Cl. ............................. 16/342; 403/97; 403/93
[58] Field of Search ........................... 16/342, 329, 330, 16/331, 332, 334, 335, 336, 344, 268, 386; 403/97, 96, 93, 92

[56] References Cited

U.S. PATENT DOCUMENTS

| | | | |
|---|---|---|---|
| 1,697,710 | 1/1929 | Bostroem | 403/97 |
| 4,186,905 | 2/1980 | Brudy | 16/342 |
| 4,506,408 | 3/1985 | Brown | 16/342 |
| 4,877,164 | 10/1989 | Baucom | 16/342 |
| 5,039,118 | 8/1991 | Huang | 403/97 |
| 5,109,572 | 5/1992 | Park | 16/334 |

*Primary Examiner*—Chuck Y. Mah
*Attorney, Agent, or Firm*—John P. O'Banion

[57] ABSTRACT

An articulating hinge assembly for pivotally coupling objects together, comprising a socket member and a cap member. A plurality of resilient prongs on the cap member reversibly engage a bore in the socket member. Outward facing barbs are included on the resilient prongs which engage a recessed region in the bore of the socket member. A plurality of serrations or grooves are included within the recessed region of the bore in the socket member. Outward facing teeth on the barbs of one or more of the resilient prongs engage and intermesh with the serrations in the recessed region of the socket member. Applying rotational force to the socket member or cap member causes the teeth to disengage the serrations and reposition within the recessed region, allowing pivotal adjustment of the cap member relative to the socket member in precise incremental units defined by the size and shape of the serrations.

17 Claims, 3 Drawing Sheets

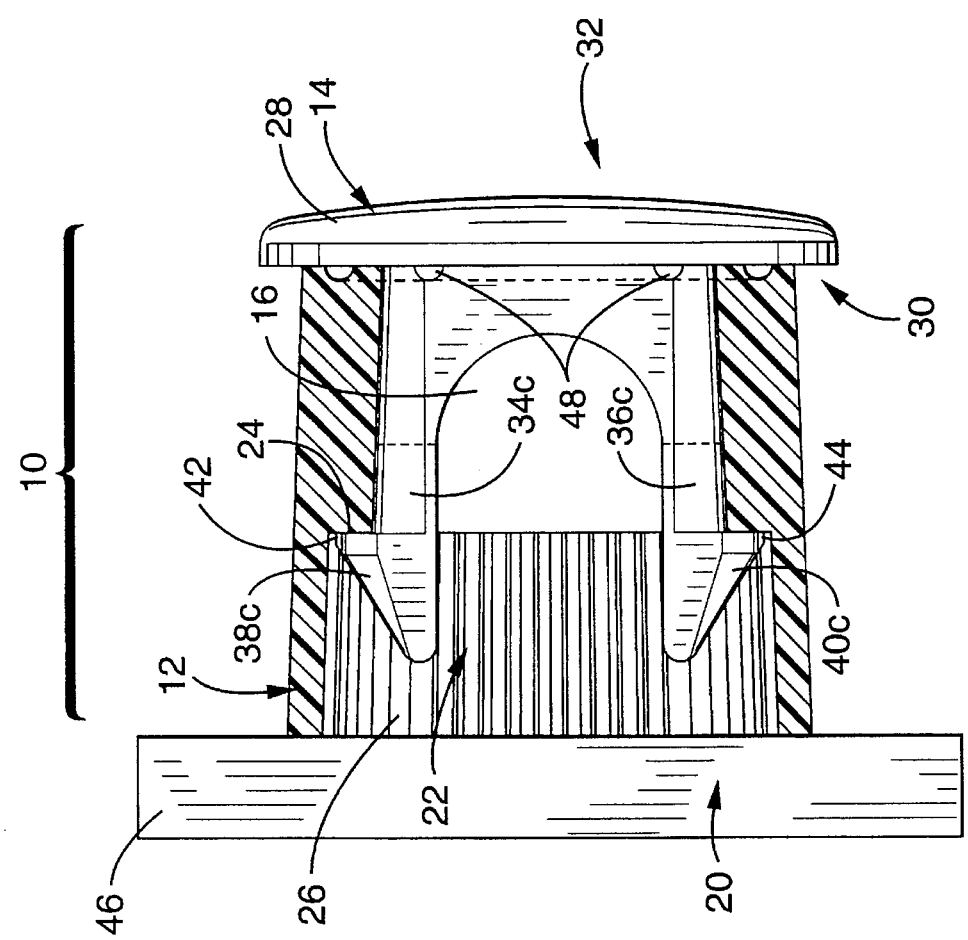
FIG. — 3

ARTICULATING HINGE ASSEMBLY

BACKGROUND OF THE INVENTION

1. Field of the Invention

This invention pertains to hinge arrangements, joints and systems for pivotally coupling two or more objects together, and more particularly to an articulating hinge assembly which provides for pivotally coupling objects together with precise, incremental ratcheting pivotal motion upon application of a small amount of force to the hinged objects.

2. Description of the Background Art

Numerous coupling systems are known which provide for pivotally coupling various objects. Many coupling systems provide for articulating pivotal movement so that coupled objects may be positioned relative to each other in incremental adjustments. Articulating coupling systems which allow incremental positional adjustment sometimes use an arrangement wherein teeth or like structures in one coupling member engage or intermesh with corresponding teeth in another coupling member. Application of force to one or both of the coupling members or the objects coupled thereto causes the teeth to disengage and reengage in a new position.

A problem with articulating coupling systems which provide such incremental adjustment occurs when such systems are used for joining together thin, resilient, highly flexible objects or objects made of materials having weak or poor mechanical properties. The amount of force necessary to cause pivotal motion in standard articulating coupling systems can be greater than the force required to deform, bend or even break a resilient or weak object or objects associated with the coupling system. This problem is illustrated by the disposable face shield devices which are increasingly used in the medical and dental professions. Generally, it is desirable for face shields to be pivotally mounted on a head-worn visor or like apparatus. The wearer of the face shield positionally adjusts the face shield by applying force to the face shield to cause pivotal motion of the face shield relative to the head-worn visor, thereby allowing the wearer to move the face shield into desired positions. Some face shields, however, are made of transparent, flexible polymeric sheet material of thin construction in order to keep material costs low. Such sheet materials are easily bent or deformed, and the force required for pivotal adjustment of a disposable face shield while using standard pivotal coupling systems generally exceeds the force necessary to bend the material of the face shield. Thus, the wearer of such a face shield cannot readily adjust the position of the face shield by pushing on the face shield, but must remove the head worn face shield and manipulate the hinge assembly directly to change the pivotal position of the face shield. The wearers of face shields, however, are frequently engaged in complex clinical procedures wherein the wearer cannot use both hands to make positional adjustments of the face shield or to remove the face shield to make such adjustments.

Accordingly, there is a need for an articulating hinge system which provides precise incremental adjustment to coupled objects upon application of a relatively small amount of force to the pivotally coupled objects, and which is suitable for use with easily bendable and easily deformable objects. The present invention satisfies these needs, as well as others, and generally overcomes the deficiencies found in the background art.

SUMMARY OF THE INVENTION

The present invention pertains to an articulating hinge assembly which allows facile pivotal adjustment in a precise incremental fashion. In general terms, the invention comprises a socket member with a plurality of internal serrations, and a cap member having a plurality of resilient prongs which insert into and engage the socket portion and are retained therein by a plurality of barbs. A tooth or protrusion provided on the barb of at least one of the plurality of resilient prongs reversibly intermeshes with the plurality of serrations in the socket member. Means for coupling to an object are included with both the socket and cap members.

By way of example and not of limitation, the socket member is of generally cylindrical structure and configuration and includes a central bore or opening which is also preferably of cylindrical configuration. The internal serrations of the socket member are longitudinally oriented and evenly spaced circumferentially about a recessed portion in the bore adjacent a back or breech end of the socket member. A circular lip or shoulder runs laterally around the circumference of the bore at the boundary of the recessed portion. The cap portion preferably includes first and second sets of prongs positioned opposite to each other, with at least one prong in each of the first and second sets. Preferably, there are three prongs each in the first and second sets of prongs, with each prong including an outward facing barb portion which engages or is received by the recessed portion in the bore of the socket member. An outward facing tooth or boss is included on the barb portion of the middle prong of each of the sets of prongs, with the tooth structured and configured to reversibly engage or intermesh with the plurality of serrations of the socket member. The means for coupling the cap member to an object and means for coupling the socket member to an object may comprise any standard coupling means. A plurality of studs or protuberances on the cap member which slidably engage an annular groove on the end of socket member may be provided if desired for detachably coupling a thin flexible sheet between the cap member and socket member, and a mounting base may be provided on the socket member for attaching the socket member to various objects or supports.

An object of the invention is to provide an articulating hinge assembly which allows precise incremental positional adjustment of pivotally coupled objects.

Another object of the invention is to provide an articulating hinge assembly which allows articulating pivotal motion upon application of a relatively small amount of force to the hinge assembly or objects coupled thereto.

Another object of the invention is to provide an articulating hinge assembly which is suitable for pivotally coupling together easily bendable or easily deformable objects.

Another object of the invention is to provide an articulating hinge assembly which allows quick detachment of pivotally coupled objects.

Another object of the invention is to provide an articulating hinge assembly which can be easily assembled and disassembled.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 3 is an assembled side view in partial cross section of the articulating hinge assembly and mounting base shown in FIG. 2.

DESCRIPTION OF THE PREFERRED EMBODIMENTS

Figure 1:
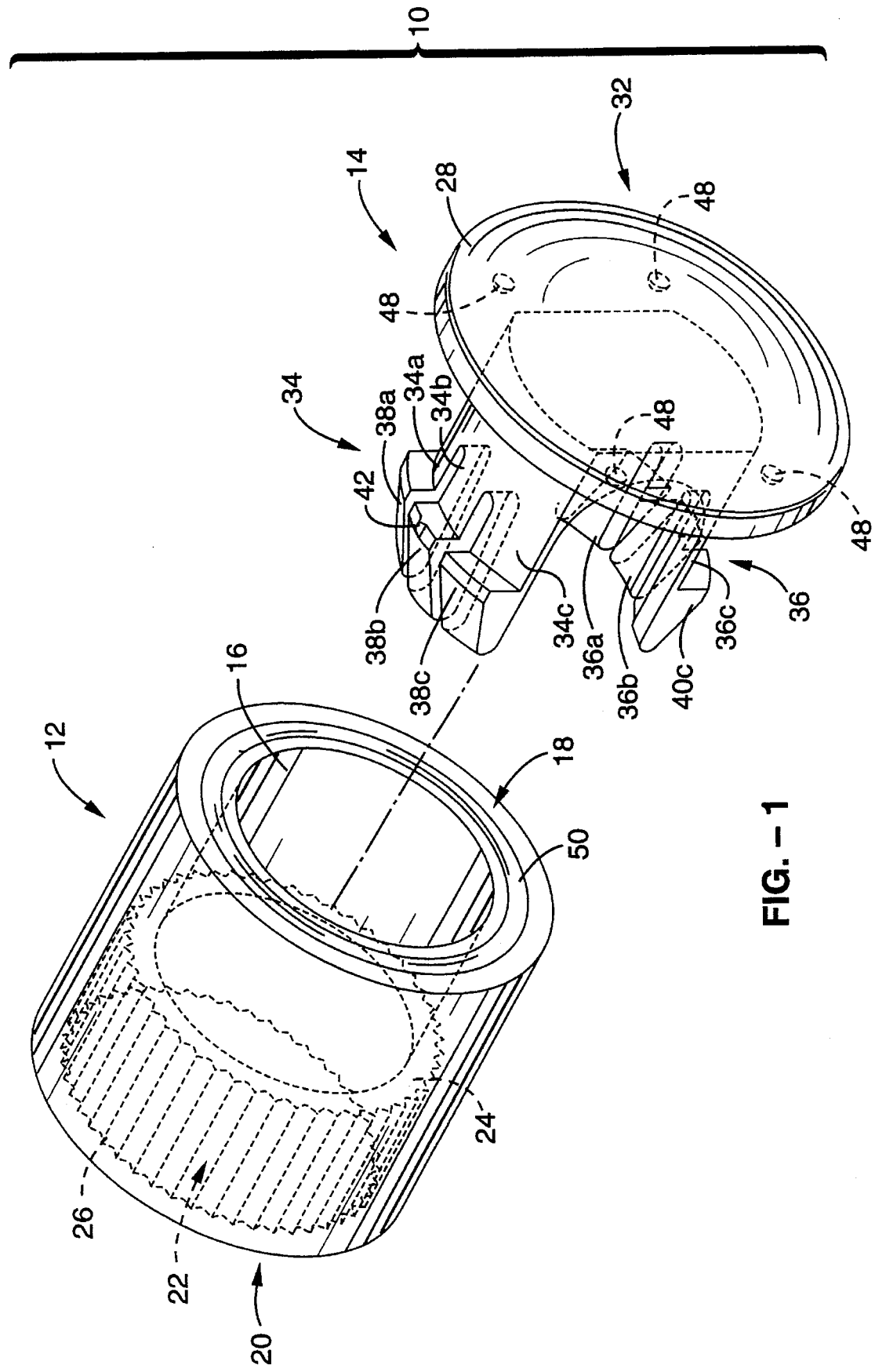
FIG. 1 is an exploded perspective view of an articulating hinge assembly in accordance with the present invention.
Figure 2:
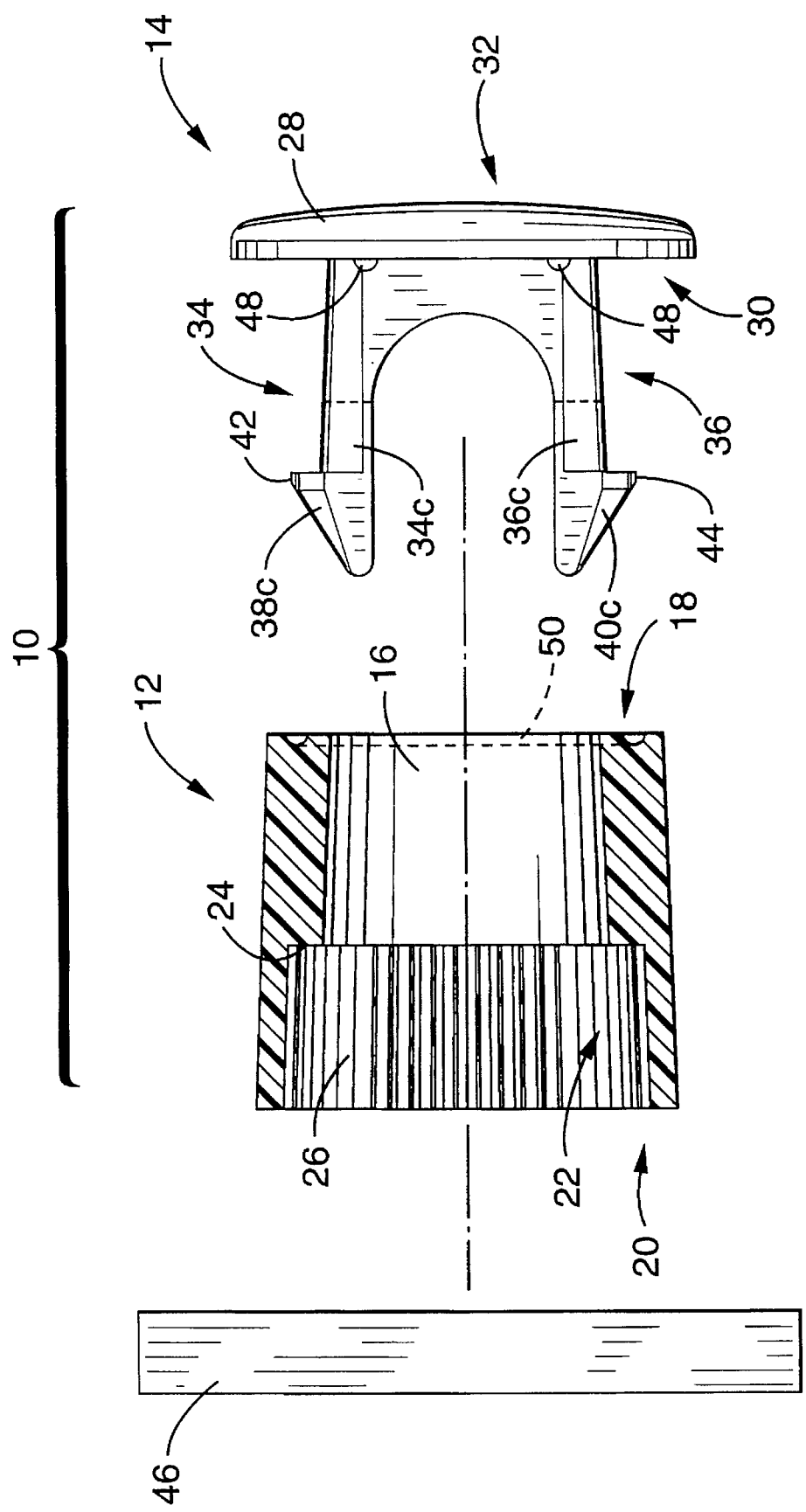
FIG. 2 is an exploded side view in partial cross-section of the articulating hinge assembly of FIG. 1 shown with a mounting base.

Referring more specifically to the drawings, for illustrative purposes the present invention is embodied in the apparatus generally shown in FIG. 1 through FIG. 3. It will be appreciated that the invention may vary as to configuration and as to details of the parts without departing from the basic concepts as disclosed herein. The invention is described in terms of pivotally coupling a thin flexible sheet of polymeric material to an object. However, it should be readily understood that the present invention may be utilized for pivotally coupling together a variety of different objects.

Referring now to FIG. 1 through FIG. 3, an articulating hinge assembly 10 in accordance with the present invention is generally shown. The invention includes a socket member 12, and a cap member 14 which reversibly and pivotally engages socket member 12 as described below. Socket member 12 includes a generally cylindrical bore 16 which preferably extends longitudinally through socket member 12 between a first or front end 18 and a second or back end 20. Bore 16 includes a generally cylindrical recessed portion or region 22 adjacent back end 20 of socket member 12, with recessed region 22 having a diameter generally greater than the diameter of bore 16, as seen most clearly in FIG. 2 and FIG. 3. A circular lip or shoulder 24 runs laterally around the circumference of bore 16 and generally defines the boundary of recessed region 22 within bore 16. A plurality of serrations, teeth, or ridges 26 are included within recessed region 22 of bore 16, and are oriented in a longitudinal direction as shown. As alternatives to serrations 26, a plurality of longitudinal grooves or channels, a knurled surface, or other common traction generating surface features may be used within recessed region 22. While socket member 12 is preferably of cylindrical or barrel-shaped configuration as shown, the external shape of socket member 12 may be varied as desired for different applications of the present invention.

Cap member 14 generally includes a disk 28 with a first or inner surface 30 and second or outer surface 32. A plurality of resilient prongs 34a, 34b, 34c, 36a, 36b, 36c are included on disk 28, and extend outward from inner surface 30 of disk in a perpendicular orientation relative to disk 28. Preferably, the plurality of prongs 34a–c and 36a–c are arranged into a first prong set 34 comprising prongs 34a–c and a second prong set 36 comprising prongs 36a–c as shown, which are arranged such that first prong set 34 is positioned generally opposite to and spaced apart from second prong set 36. First prong set 34 preferably includes three prongs, with a central or middle prong 34b and outer prongs 34a, 34c. Second prong set 36 likewise preferably includes a central or middle prong 36b interposed between outer prongs 36a, 36c. Prongs 34a, 34b, 34c each have an outward facing barb 38a, 38b, 38c respectively, and prongs 36a, 36b, 36c each have an outward facing barb 40a, 40b, 40c respectively. Barbs 38a–c are oriented or pointed in a direction generally opposite to that of barbs 40a–c. Barbs 38a–c and 40a–c preferably are tapered in shape, with the taper extending in the direction away from disk 28. An outward facing tooth, boss, or projection 42 is provided on barb 38b of central prong 34b of first set 34, and a corresponding outward facing tooth or projection 44 is included on barb 40b of central prong 36b of second set 36.

Prongs 34a–c, 36a–c are structured and configured to fit within cylindrical bore 16, and barbs 38a–c, 40a–c are structured and configured to fit within cylindrical recessed region 22 of bore 16. First and second prong sets 34, 36 are generally spaced apart such that the distance between the outside facing edges of prong sets 34, 36 is generally equal to the diameter of bore 16. The distance between the outermost tips of barbs 38a–c of first prong set 34 and the outermost tips of barbs 40a–c of second prong set 36 is generally equal to the diameter of recessed region 22. Teeth 42, 44 are generally structured and configured to engage and intermesh with serrations 26 in recessed region 22, as discussed further below. Outer prongs 34a, 34c and corresponding barbs 38a, 38c preferably are rounded on the corners as shown, to conform to the cylindrical shape of bore 16 and recessed region 22 and to facilitate insertion into bore 16 and recessed region 22. Outer prongs 36a, 36c and corresponding barbs 40a, 40c likewise are preferably rounded on the corners.

The arrangement of the plurality of prongs 34a–c, 36a–c on cap member 12 as shown in FIG. 1 through FIG. 3 and as described herein should not be considered as limiting. Numerous alternative prong configurations may be used with the invention. A larger or smaller number of resilient prongs than the six prongs 34a–c, 36a–c related above may be used in association with cap member, and the prongs need not be arranged in opposing sets. For example, a single pair of opposing, spaced apart prongs may be utilized with the invention, with outward facing barbs on each prong, and an outward facing tooth included on the barb of each prong. Alternatively, a plurality of prongs may be arranged in a circular arrangement corresponding generally to the circumference of bore 16, without any arrangement of the prongs into sets as described above. Likewise, the location and number of teeth 42, 44 may be varied with the invention, and need not be located on a central prong. However, at least one tooth is generally included on at least one of a plurality of prongs on cap member 14. Disk 28 may alternatively comprise a knob suitable for hand-manipulation, or a member of any desired shape or configuration as required for particular applications of the invention.

Means for coupling socket member 12 to an object and means for coupling cap member 14 to an object are preferably included with the invention, to allow various objects to be pivotally coupled together by articulating hinge system 10. As shown in FIG. 2 and FIG. 3, the coupling means associated with socket member 12 may comprise a mounting base 46 included adjacent back end 20 of socket member 12. Mounting base 46 may be coupled to various objects such as a head band or visor apparatus by adhesives, clips, clamps, screws, VELCRO® type hook and loop fasteners, snap fitting arrangements, or other standard coupling means. Outer surface 32 of cap member 14 may likewise be utilized for coupling to various objects by use of adhesives or like attachment means. Socket member 12 and cap member 14 as shown in FIG. 1 through FIG. 3 are structured and configured to allow detachable coupling to cap member 28 of a thin sheet (not shown) of resilient polymeric material of the sort commonly used for face shields. A plurality of studs or protuberances 48 are provided on inner surface 30 of cap member 14 as coupling means, with studs 48 slidably associating with a circular or annular groove 50 on front end 18 of socket member 12 when cap member and socket member are engaged together. A plurality of holes corresponding to the arrangement of studs 48 would be included in the thin sheet to allow snap fitting attachment of the sheet to cap member 28 via studs 48.

The articulating hinge assembly 10 is utilized generally by coupling an object to socket member 12 by mounting base 46 or other coupling means associated with socket member 12, coupling an object to cap member 14 by studs 48 or other coupling means, and then inserting the plurality of resilient prongs 34a–c, 36a–c into bore 16 to engage socket member 12 and cap member 14 together, with barbs 38a–c, 40a–c snap fitting over lip 24 into recessed region 22 to retain cap member 14 and socket member 12 together. As mentioned above, the distance between the outermost tips of barbs 38a–c of first prong set 34 and the outermost tips of barbs 40a–c of second prong set 36 is generally equal to the diameter of cylindrical recessed region 22, and the diameter of recessed region 22 is greater than the diameter of bore 16. Thus, the distance between the outermost tips of barbs 38a–c of first prong set 34 and the outermost tips of barbs 40a–c of second prong set 36 is greater than the diameter of bore 16, and force must be applied to cap member 14 in order for barbs 38a–c, 40a–c to be inserted through bore 16 in order to reach recessed region 22. The tapered shape of barbs 38a–c, 40a–c allow the barbs to be inserted into bore 16, and resilient prongs 34a–c, 36a–c bend inward as barbs 38a–c, 40a–c are inserted through bore 16. As barbs 38a–c, 40a–c clear lip 24, resilient prongs 34a–c, 36a–c return to their relaxed positions, so that barbs 38a–c, 40a–c snap fit over lip 24 into recessed region 22 and are retained therein. Outward facing teeth 42, 44 interfit between adjacent serrations 26 while barbs 38a–c, 40a–c are positioned within recessed region 22.

The disk 28 and plurality of prongs 34a–c, 36a–c of cap member 14 are preferably integral portions of a single piece of resilient, durable polymeric material such as an engineering resin, or resilient metal or metallic alloy. Socket member 12 is likewise preferably fabricated from a durable polymeric material.

By applying a rotational force to cap member 14 or socket member 12 while cap member 14 and socket member 12 are joined together as described above, cap member 14 rotates or pivots relative to socket member 12. As cap member 14 rotates relative to socket member 12, prongs 34a–c, 36a–c correspondingly move within bore 16, and barbs 38a–c, 40a–c undergo corresponding movement within recessed region 22. During such rotational motion, teeth 42, 44 disengage serrations 26, due to the resilient nature of central prongs 34b, 36b to which teeth 42, 44 are associated, allowing cap member 14 to be pivotally adjusted relative to socket member 12 in precise incremental units defined generally by the distance between serrations 26 within recessed region 22. Thus, cap member 14 pivots or articulates relative to socket member 12 in a ratchet-like fashion as teeth 42, 44 move relative to serrations 26. The size or degree of the incremental units of pivotal adjustment available with the present invention may be tailored as required by varying the distance between serrations 26. In situations wherein a high degree of accuracy of articulating movement is required, serrations 26 preferably are narrowly spaced apart, and teeth 42, 44 are correspondingly structured and configured to interfit between the serrations 26.

The force required to cause cap member 14 to rotate or pivot relative to socket member 12 when cap member 14 and socket member 12 are joined together is relatively small because of the small contact area of teeth 42, 44 with serrations 26 and the resilient nature of prongs 34b, 36b to which teeth 42, 44 are attached. The amount of force required for articulation of the hinge assembly 10 can be tailored by increasing or decreasing the thickness, and thus the resiliency, of the prongs 34b, 36b to which teeth 42, 44 are coupled, by increasing or decreasing the size of teeth 42, 44, by varying the size of serrations 26, or by fabricating the prongs from material having greater or lesser resiliency.

The articulating hinge assembly 10 can be readily disassembled by reaching into recessed region 22 of socket member 12 through back end 20, either by using a person's fingers or with a suitable tool, and pushing prongs 34a–c towards prongs 36a–c. As the resilient prongs are compressed, barbs 38a–c, 40a–c disengage lip or shoulder 24 and allow cap member 14 to be disengaged from socket member 12. A hole (not shown) may be included in mounting base 46 to allow access to prongs 34a–c, 36a–c through back end 20 of socket member 12.

The present invention is particularly useful as an articulating hinge arrangement for thin face shield devices, as mentioned-above, because the relatively small amount of force required to cause pivotal articulation of cap member 14 relative to socket member 12. In order to provide face shields which are sufficiently low in cost to allow frequent disposal and replacement, the face shields generally must be fabricated from relatively thin transparent polymer sheet materials such as acrylic, polycarbonate, polyethylene terephthalate, or like transparent polymeric materials. Face shields made from such materials, although inexpensive, have mechanical properties which make the face shields easy to bend, twist or otherwise deform when force is applied to the face shield, due to the thin construction of the shield.

To use the invention with a thin, flexible face shield (not shown), a pair of socket members 12 would be mounted on the head band portion of a conventional visor apparatus (not shown) by base mounts 46, and the corners of the thin, flexible face shield would each be coupled to one of a pair of cap members 14 through use of studs 48 or by other standard coupling means. A face shield may be coupled to cap member 14 via studs 48 by providing a suitable pattern of holes in the corners of the thin polymer sheet of the face shield which match the arrangement of studs 48 in cap member, so that the face shield may be snap fitted onto cap member 14 by studs 48 and held between cap member 14 and socket member 12 when studs 48 slidably engage groove 50. While a person is wearing a face shield apparatus using the invention, the face shield may be pivotally adjusted by pushing or applying force to the face shield with the wearer's hands to cause cap member 14 to rotate relative to socket member 12 as related above. Since only a relatively small amount of force is required for articulation of the hinge assembly 10, pushing on the thin face shield material will result in the desired articulation rather than bending of the face shield. The face shield may be removed from the articulating hinge assembly 10 and replaced by disengaging cap member 14 from socket member 12 as described above, and removing the face shield from studs 48.

Accordingly, it will be seen that this invention provides an articulating hinge assembly which allows pivotal adjustment in precise increments, which requires application of a relatively small amount of force in order to achieve articulating pivotal motion, and which can be easily assembled and disassembled. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An articulating hinge assembly, comprising:
   (a) a socket member, said socket member including a bore, said bore including a recessed region, said socket member having a plurality of serrations located in said recessed region of said bore; and
   (b) a cap member, said cap member including a plurality of resilient prongs, at least one said prong including an outward facing barb, at least one said barb including an outward facing tooth.

2. An articulating hinge assembly as recited in claim 1, wherein said plurality of prongs comprise first and second opposing sets of said prongs.

3. An articulating hinge assembly as recited in claim 2, wherein each said set of prongs includes a central prong and a pair of outer prongs, each said central prong including an outward facing barb having an outward facing tooth.

4. An articulating hinge assembly as recited in claim 1, wherein said serrations are longitudinally oriented and evenly spaced about the circumference of said recessed region of said bore.

5. An articulating hinge assembly as recited in claim 1, further comprising a circular lip within said bore of said socket member, said circular lip defining a boundary for said recessed region.

6. An articulating hinge assembly as recited in claim 1, further comprising:
   (a) means for coupling said socket member to an object; and
   (b) means for coupling said cap member to an object.

7. An articulating hinge assembly, comprising:
   (a) a socket member, said socket member including a cylindrical bore, said bore including a recessed region;
   (b) said socket member including a plurality of serrations, said serrations located in said recessed region of said bore; and
   (c) a cap member, said cap member including a plurality prongs, each said prong having an outward facing barb, at least one said barb having an outward facing tooth.

8. An articulating hinge assembly as recited in claim 7, wherein said plurality of prongs comprises first and second sets of opposing prongs, each said set of prongs including a central prong and a pair of outer prongs, each said central prong including one said outward facing tooth.

9. An articulating hinge assembly as recited in claim 7, wherein said serrations are longitudinally oriented and evenly spaced about the circumference of said recessed region.

10. An articulating hinge assembly as recited in claim 7, further comprising a circular lip extending laterally about said bore of said socket member, said circular lip defining a boundary for said recessed region.

11. An articulating hinge assembly as recited in claim 7, further comprising:
    (a) means for coupling said socket member to an object; and
    (b) means for coupling said cap member to an object.

12. An articulating hinge assembly, comprising:
    (a) a socket member, said socket member having first and second ends, said socket member including a cylindrical bore, said cylindrical bore extending longitudinally between said first and second ends, said cylindrical bore including a recessed region, said cylindrical bore having a lateral lip extending around the circumference of said bore, said lateral lip defining a boundary for said recessed region;
    (b) said socket member including a plurality of inward facing serrations, said serrations located in said recessed region of said bore, said serrations longitudinally oriented and evenly spaced about the circumference of said recessed region; and
    (c) a cap member, said cap member including first and second opposing sets of prongs, each said set including a central prong and a pair of outer prongs, each said prong including an outward facing barb, said barb of said central prong in each said set of prongs including an outward facing tooth.

13. An articulating hinge assembly as recited in claim 12, further comprising:
    (a) means for coupling said socket member to an object; and
    (b) means for coupling said cap member to an object.

14. An articulating hinge assembly as recited in claim 13, wherein said cap member includes a disk, said disk coupled to said plurality of prongs, said disk substantially perpendicular to said plurality of prongs.

15. An articulating hinge assembly as recited in claim 14, wherein said coupling means for said socket member further comprises a mounting base, said mounting base associated with said second end of said socket member.

16. An articulating hinge assembly as recited in claim 15, wherein said coupling means for said cap member comprises a plurality of studs, said studs included on an inner face of said disk.

17. An articulating hinge assembly as recited in claim 16, wherein said socket member includes an annular groove, said annular groove included on said first end of said socket member, said annular groove structured and configured to slidably receive said plurality of studs on said disk of said cap member.

\* \* \* \* \*